United States Patent
Fix et al.

(10) Patent No.: US 9,506,392 B2
(45) Date of Patent: Nov. 29, 2016

(54) EXHAUST GAS GUIDE ELEMENT, EXHAUST GAS MEASURING DEVICE FOR A VEHICLE, AND METHOD FOR PRODUCING AN EXHAUST GAS GUIDE ELEMENT

(71) Applicant: Robert Bosch GmbH, Stuttgart (DE)

(72) Inventors: Richard Fix, Gerlingen (DE); Andreas Krauss, Teubingen (DE); Markus Widenmeyer, Shoenaich (DE)

(73) Assignee: Robert Bosch GmbH, Stuttgart (DE)

( * ) Notice: Subject to any disclaimer, the term of this patent is extended or adjusted under 35 U.S.C. 154(b) by 170 days.

(21) Appl. No.: 14/217,569

(22) Filed: Mar. 18, 2014

(65) Prior Publication Data

US 2015/0267595 A1 Sep. 24, 2015

(30) Foreign Application Priority Data

Mar. 19, 2013 (DE) ......................... 10 2013 204 780

(51) Int. Cl.
*G01M 15/10* (2006.01)
*F01N 13/08* (2010.01)
*F01N 11/00* (2006.01)
*F01N 13/00* (2010.01)

(52) U.S. Cl.
CPC ............... *F01N 13/08* (2013.01); *F01N 11/00* (2013.01); *F01N 13/008* (2013.01)

(58) Field of Classification Search
CPC ..... G01M 15/10; F01N 11/00; F01N 13/008
USPC ............... 73/114.69, 114.71, 114.72, 114.73
See application file for complete search history.

(56) References Cited

U.S. PATENT DOCUMENTS

| | | | | | |
|---|---|---|---|---|---|
| 4,534,213 | A | * | 8/1985 | Mirikidani ................. | 73/114.71 |
| 5,616,825 | A | * | 4/1997 | Achey et al. ............... | 73/23.31 |
| 5,621,166 | A | * | 4/1997 | Butler ................. | G01M 15/108 250/338.5 |
| 5,993,743 | A | * | 11/1999 | Nordman ............. | G01N 1/2252 250/339.13 |
| 7,739,898 | B2 | * | 6/2010 | Shaddock ............... | F01N 13/08 73/23.31 |
| 9,188,506 | B2 | * | 11/2015 | Asano ................... | G01N 1/2252 |
| 2005/0257605 | A1 | * | 11/2005 | Colvin ...................... | G01F 1/88 73/114.76 |
| 2006/0065041 | A1 | * | 3/2006 | Kono et al. .................. | 73/23.32 |
| 2006/0288759 | A1 | * | 12/2006 | Okumura et al. ........... | 73/31.05 |
| 2007/0204597 | A1 | * | 9/2007 | Nakano .......................... | 60/276 |
| 2009/0217745 | A1 | * | 9/2009 | Schneider et al. ......... | 73/114.71 |
| 2010/0300175 | A1 | * | 12/2010 | Hokamura ......... | G01N 33/0006 73/1.06 |
| 2013/0125533 | A1 | * | 5/2013 | Sullivan .................. | F01N 11/00 60/276 |
| 2013/0136656 | A1 | * | 5/2013 | Okada ................ | G01N 33/0004 422/52 |
| 2013/0174641 | A1 | * | 7/2013 | Asano .................. | G01N 1/2252 73/23.31 |
| 2014/0261348 | A1 | * | 9/2014 | Wahl et al. .................... | 123/672 |

FOREIGN PATENT DOCUMENTS

DE 10 2007 040 726 A1 3/2009

* cited by examiner

*Primary Examiner* — Eric S McCall
(74) *Attorney, Agent, or Firm* — Maginot, Moore & Beck LLP

(57) ABSTRACT

An exhaust gas guide element for conducting at least a portion of an exhaust gas to a sensor for a vehicle. The exhaust gas guide element has a greater extent in a direction of a longitudinal axis than in a direction of a transverse axis, and is gas-permeable along the direction of the longitudinal axis. One end of the gas guide element along the direction of the longitudinal axis is configured as a receiving region, and the opposite end is configured as a measuring region. A sensor can be positioned in the measuring region, and a gas receiving element is positioned in the receiving region.

9 Claims, 2 Drawing Sheets

EXHAUST GAS GUIDE ELEMENT, EXHAUST GAS MEASURING DEVICE FOR A VEHICLE, AND METHOD FOR PRODUCING AN EXHAUST GAS GUIDE ELEMENT

This application claims priority under 35 U.S.C. §119 to patent application no. DE 10 2013 204 780.0, filed on Mar. 19, 2013 in Germany, the disclosure of which is incorporated herein by reference in its entirety.

BACKGROUND

The present disclosure relates to an exhaust gas guide element for conducting at least a portion of an exhaust gas to a sensor, to a corresponding exhaust gas measuring device, and also to a corresponding method for producing an exhaust gas guide element for conducting at least a portion of an exhaust gas to an exhaust gas sensor.

In existing exhaust gas sensors, the generally electrically heated, ceramic sensor element is exposed directly to the exhaust gas which is to be analyzed. For a newly developed generation of exhaust gas sensors of which the sensor element is designed as a miniature component in a very small installation space in cubic form (as is described in DE102007040726 for example), the main requirements of the installation are as follows:

the operating temperature of novel, miniaturized sensor elements can lie below the temperature of existing sensors and therefore below the maximum exhaust gas temperature. During operation, the sensor should be electrically heated and the temperature controlled to prespecified values in this way. If the exhaust gas temperature at specific operating points of the motor is higher than the operating temperature of the sensor, the installation has to ensure a lower operating temperature at the site of the sensor than the exhaust gas temperature. (In the case of the sensors which have been commercially available to date, a minimum temperature has to be reached, a higher gas temperature is not critical for the sensor element and, in the sense of a lower heating power requirement, is rather desired).

Electrical contact has to be made with the sensor element and said sensor element has to be mechanically fixed. The requirements in respect of the dynamics of the sensor are dependent on the substances which are to be detected by the sensor. Gas should generally be transported to the sensor without delay as far as possible.

SUMMARY

Against this background, the present disclosure presents an exhaust gas guide element for conducting at least a portion of an exhaust gas to a sensor, furthermore an exhaust gas measuring device which uses this exhaust gas guide element, and also finally a corresponding method for producing an exhaust gas guide element for conducting at least a portion of an exhaust gas to an exhaust gas sensor. Advantageous refinements can be found in the claims and the following description.

An exhaust gas guide element for conducting at least a portion of an exhaust gas to a sensor has a greater extent in a direction of a first longitudinal axis than in the direction of a transverse axis, wherein the exhaust gas guide element is gas-permeable along the direction of the longitudinal axis, wherein an end along the direction of the longitudinal axis is designed as a receiving region and the opposite end is designed as a measuring region, wherein, in particular, a sensor can be arranged in the measuring region, wherein a gas receiving element is arranged in the receiving region.

An exhaust gas guide element can be understood to be a gas-permeable support element for a sensor, in particular an exhaust gas sensor. An extent can be understood to be a dimension or length of the exhaust gas guide element. A longitudinal axis can be understood to be an axis or direction in which the exhaust gas guide element has a greatest possible length. A transverse axis can be understood to be an extent or length in which the exhaust gas guide element has a shortest possible length. The exhaust gas guide element can be designed to conduct at least a portion of an exhaust gas along its longitudinal axis. In this case, the portion of the exhaust gas can be received in the receiving region of the exhaust gas guide element and conducted to the measuring region. In this case, a gas receiving element is arranged in the receiving region. The gas receiving element can be designed to conduct a portion of the exhaust gas in an exhaust gas stream from the exhaust gas stream into the exhaust gas guide element. The gas receiving element can be called a functional element. The portion of the exhaust gas which is conducted into the exhaust gas guide element by the gas receiving element can be conducted into the exhaust gas guide element in the direction of the measuring region. A sensor can be understood to be a sensor element and/or an exhaust gas sensor which provides, for example, an electrical signal which represents a physical variable such as a gas concentration in the exhaust gas. Thermal and chemical requirements of modern sensors can advantageously be met by an arrangement of the sensors physically offset in relation to an exhaust gas stream and a reduction to a portion of the exhaust gas stream.

Furthermore, in one embodiment, the exhaust gas guide element can also be arranged in an exhaust gas sensor housing. The exhaust gas sensor housing can be arranged in a guide device of an exhaust gas stream. In this case, a subregion of the exhaust gas sensor housing, in which the receiving region of the exhaust gas guide element is arranged, can be arranged in the exhaust gas stream within the guide device of the exhaust gas stream. In this case, a further subregion of the exhaust gas sensor housing, in which the measuring region of the exhaust gas guide element is arranged, can be arranged outside the exhaust gas stream.

According to one embodiment, the receiving region can be arranged within a guide device of an exhaust gas stream and the measuring region can be arranged outside a guide device of an exhaust gas stream. In this case, at least a portion of the exhaust gas can be conducted by the exhaust gas guide element from within the guide device of the exhaust gas stream to outside the guide device of the exhaust gas stream. A guide device of the exhaust gas stream can be understood to be an exhaust gas section or a portion of an exhaust gas section of a vehicle (for example the exhaust system). An arrangement of this kind can allow a portion of the exhaust gas to be conducted from the exhaust gas stream, via the receiving region, to the measuring region. A temperature of the exhaust gas in the measuring region can be distinguished from a temperature of the exhaust gas in the receiving region or in the exhaust gas stream by an arrangement of this kind. In particular, a lower temperature than in the exhaust gas stream can be set in the measuring region by the exhaust gas guide element.

At least one channel can be integrated into the exhaust gas guide element. As an alternative or in addition, at least one cavity can be integrated into the exhaust gas guide element. As an alternative or in addition, at least one chamber can be integrated into the exhaust gas guide element. As an alternative or in addition, at least one porous region can be integrated into the exhaust gas guide element. At least as an alternative or in addition, a conductor track can be integrated into the exhaust gas guide element. At least one heating element can be integrated into the exhaust gas guide element. In addition, metal and/or ceramic semi-finished products can be integrated into the exhaust gas guide element, in particular at least one ceramic tube. An embodiment of this type provides the advantage of particularly good and rapid guiding or conducting of the exhaust gas in the exhaust gas guide element.

According to one embodiment of the, the exhaust gas guide element has at least one electrical conductor. In this case, electrical contact can be made with the gas receiving element in the receiving region and, at the same time or as an alternative, with a sensor in the measuring region using the at least one electrical conductor. Furthermore, the exhaust gas guide element can have at least two electrical conductors. An electrical conductor which is integrated into the exhaust gas guide element can replace an external, additional cabling arrangement. Contact can be made with a sensor which is arranged in the measuring region and, at the same time or as an alternative, with the gas receiving element in the receiving region using an electrical line or, as an alternative, using a plurality of electrical lines. For example, the gas receiving element can be electrically connected to a sensor which is arranged in the measuring region. It may be advantageous to extend the exhaust gas guide element and/or the at least one electrical conductor beyond the measuring region in order, for example, to allow connection and/or contact to be made in a pluggable manner. As a result, a sensor which is arranged in the measuring region and/or the gas receiving element can be connected to a controller externally to the exhaust gas guide element.

Furthermore, the gas receiving element can be designed as a particle filter. As an alternative or in addition, the gas receiving element can also be designed as a diffusion barrier. As an alternative or in addition, it is further feasible for the gas receiving element to be designed as a pump element. As an alternative or in addition, the gas receiving element can further be designed to change the temperature of a portion of the exhaust gas which is conducted into the exhaust gas guide element. An embodiment of the present disclosure in which the gas receiving element is designed as an element for capturing or filtering predetermined gas constituent parts as an alternative or in addition is further expedient. As an alternative or in addition, the gas receiving element can further be designed to catalytically convert the portion of the exhaust gas which is conducted into the exhaust gas guide element, for example using a catalytic converter. The catalytic converter can be heated.

For the purpose of improving the functioning and/or stability of the exhaust gas sensor element, it may be advantageous to connect additional functions upstream by means of the gas receiving element, such as filters, diffusion barriers, catalytic converters, getter materials, Nernst cells, pump elements for example, which change the gas composition of the partial quantity of the exhaust gas stream which is to be measured before said quantity reaches the sensor. An embodiment of the gas receiving element of this kind may require a different temperature to the, in particular miniaturized, sensor, with the result that thermal separation between exhaust gas section/exhaust gas stream and sensor may be required. The described embodiments can advantageously protect against droplet impact and particle impact and also provide resistance against soiling by, for example, soot.

An exhaust gas measuring device for a vehicle comprises:
an exhaust gas guide element for conducting at least a portion of an exhaust gas to an exhaust gas sensor for a vehicle; and
a sensor which is arranged in the measuring region of the exhaust gas guide element and, at the same time or as an alternative, an exhaust gas sensor housing which can be arranged in a guide device of an exhaust gas stream, wherein the exhaust gas guide element is arranged in the exhaust gas sensor housing, wherein a subregion of the exhaust gas sensor housing, in which the receiving region of the exhaust gas guide element is arranged, can be arranged in the exhaust gas stream, wherein a further subregion of the exhaust gas sensor housing, in which the measuring region of the exhaust gas guide element is arranged, can be arranged outside the exhaust gas stream.

According to one embodiment, a sensor can be arranged in the measuring region of the exhaust gas guide element. In this case, the sensor can be designed as a field-effect-based gas sensor. In this case, the sensor can be designed as a miniaturized electrochemical sensor. The field-effect-based gas sensor can be produced on the basis of silicon (Si), silicon carbide (SiC) or gallium nitride (GaN).

Furthermore, a semiconductor sensor can be arranged in the measuring region. When a semiconductor sensor, or a sensor which is produced using semiconductor process technology, is used, a microelectronics system can be integrated into the sensor in one embodiment. In this case, sensor signals can be conditioned directly in the sensor. When the sensor is connected to the gas receiving element by means of at least one electrical line, a microelectronics system which is integrated in the sensor can control and/or regulate and/or measure a function in the gas receiving element.

According to one embodiment, a sensor can be arranged in the measuring region. The sensor can be directly coupled to a microelectronics system. A microelectronic evaluation unit can be integrated into the sensor. In the present case, a microelectronics system or a microelectronic evaluation unit can be understood to be an electrical device which processes sensor signals and outputs control and/or data signals depending on the sensor signals. The microelectronics system or microelectronic evaluation unit can have an interface which can be designed using hardware and/or software. In the case of design using hardware, the interfaces can be, for example, part of a so-called system ASIC which contains a wide variety of functions of the apparatus. However, it is also possible for the interfaces to be dedicated, integrated circuits or to at least partially comprise discrete components. In the case of design using software, the interfaces can be software modules which are present, for example, on a microcontroller together with other software modules.

A method for producing an exhaust gas guide element for conducting at least a portion of the exhaust gas to an exhaust gas sensor for a vehicle is further presented here, wherein the method comprises the following steps:
providing a gas receiving element and also an exhaust gas guide element which has a greater extent in a direction of a longitudinal axis than in the direction of a transverse axis, wherein the exhaust gas guide element is gas-permeable along the direction of the longitudinal axis, wherein one end along the direction of the longitudinal axis is designed as a receiving region and the opposite end is designed as a measuring region, wherein, in particular, a sensor can be arranged in the measuring region; and arranging the gas receiving element in the receiving region of the exhaust gas guide element.

It is also expedient when the exhaust gas guide element is produced using a production method involving thick-film technology. It is also expedient when the exhaust gas guide element is produced thin-film technology, as an alternative. It is also expedient when the exhaust gas guide element is produced by means of microsystem process engineering. The thick-film technology may be ceramic thick-film technology, for example on the basis of zirconium (IV) oxide ($ZrO_2$), aluminum oxide ($Al_2O_3$) or low-temperature co-fired ceramic technology (LTCC). The thin-film technology can be based on silicon (Si). The microsystem process engineering can also be understood to be MEMS process engineering based on the term "micro-electro-mechanical systems".

BRIEF DESCRIPTION OF THE DRAWINGS

The disclosure will be explained in greater detail by way of example below with reference to the appended drawings, in which.

DETAILED DESCRIPTION

In the following description of preferred exemplary embodiments of the present disclosure, identical or similar reference symbols will be used for the elements which are illustrated in the various figures and act in a similar manner, in which case repeated description of said elements is dispensed with.

Figure 1:
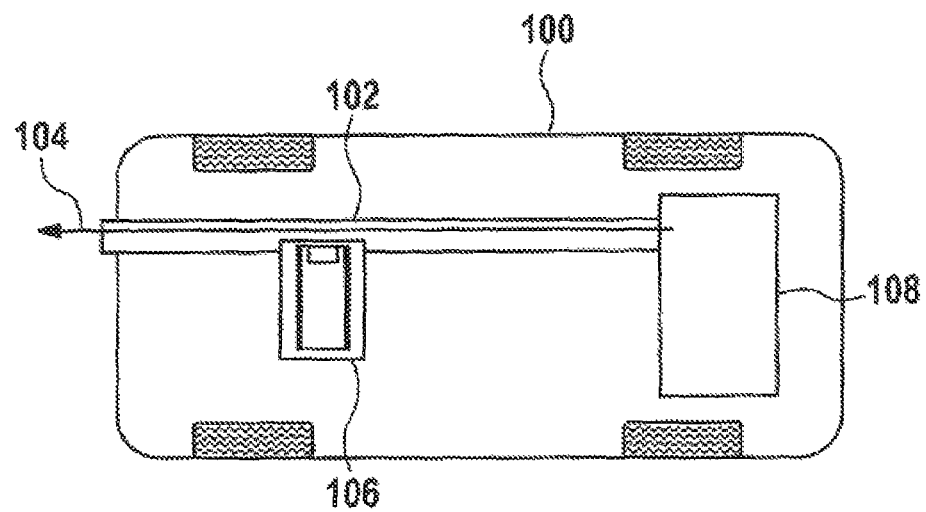
FIG. 1 shows a schematic illustration of a vehicle having a guide device for the exhaust gas stream and an exhaust gas measuring device according to one exemplary embodiment of the present disclosure.

FIG. 1 shows a schematic illustration of a vehicle 100 having a guide device 102 of the exhaust gas stream 104 and an exhaust gas measuring device 106 according to one exemplary embodiment of the present disclosure. A vehicle 100 has an internal combustion engine 108. The exhaust gases produced in said internal combustion engine are conducted away from the internal combustion engine 108 as exhaust gas stream 104 using a guide device 102 for the exhaust gas stream 104. In the exemplary embodiment shown, the internal combustion engine 108 is arranged in the region of the front of the vehicle, the guide device 102 for the exhaust gas stream 104 extending from the internal combustion engine 108, along the vehicle 100, to the rear of the vehicle 100. The exhaust gas stream 104 is discharged to the atmosphere at said rear of the vehicle. In other exemplary embodiments, the internal combustion engine 108 and the guide device 102 for the exhaust gas stream 104 can be arranged differently. For example, the internal combustion engine can be arranged, for example, in the center of the vehicle or in the region of the rear of the vehicle. The guide device 102 for the exhaust gas stream can conduct, for example, the exhaust gas stream 104 in the direction of the rear of the vehicle or to one side of the vehicle. An exhaust gas measuring device 106 is arranged on the guide device 102 for the exhaust gas stream 104. A portion of the exhaust gas measuring device 106 is arranged within the guide device 102 for the exhaust gas stream 104, and in the process is directly exposed to the exhaust gas stream 104. A further portion of the exhaust gas measuring device 106 is arranged outside the guide device 102 for the exhaust gas stream 104. The exhaust gas measuring device 106 can have an exhaust gas guide element, as will be described in FIG. 2 which follows.

Figure 2:
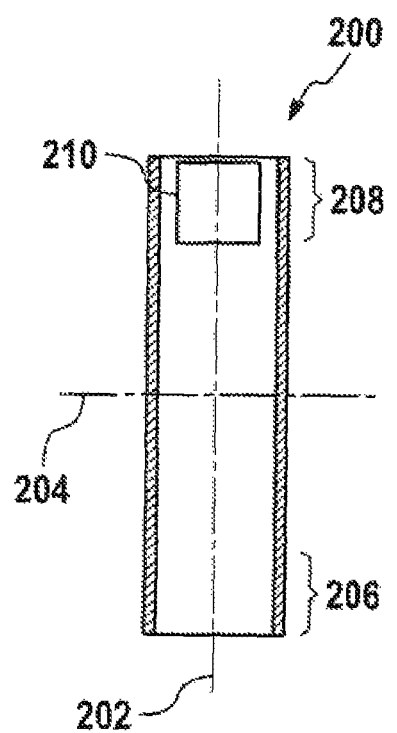
FIG. 2 shows a schematic illustration of an exhaust gas guide element according to one exemplary embodiment of the present disclosure.

FIG. 2 shows a schematic illustration of an exhaust gas guide element 200 according to one exemplary embodiment of the present disclosure. The exhaust gas guide element 200 has an elongate shape. For example, the exhaust gas guide element 200 has a larger extent along a first longitudinal axis 202 than along a transverse axis 204. A subsection along the longitudinal axis 202 is designed as a measuring region 206. The measuring region 206 is arranged at one end of the exhaust gas guide element 200. A receiving region 208 is arranged at that end of the exhaust gas guide element 200 which is situated opposite the measuring region 206. A gas receiving element 210 is arranged within the receiving region 208. The exhaust gas guide element 200 is gas-permeable in its longitudinal direction, that is to say along the longitudinal axis 202. By way of example, in one exemplary embodiment, the exhaust gas guide element 200 can be designed in a tubular manner. The measuring region 206 is designed such that a sensor, in particular a gas sensor, can be arranged here. Depending on the exemplary embodiment, the sensor can be arranged within or outside the exhaust gas guide element 200. In one exemplary embodiment, a portion of the sensor can be arranged within the exhaust gas guide element 200 and another portion of the sensor can be arranged outside the exhaust gas guide element 200.

Figure 3:
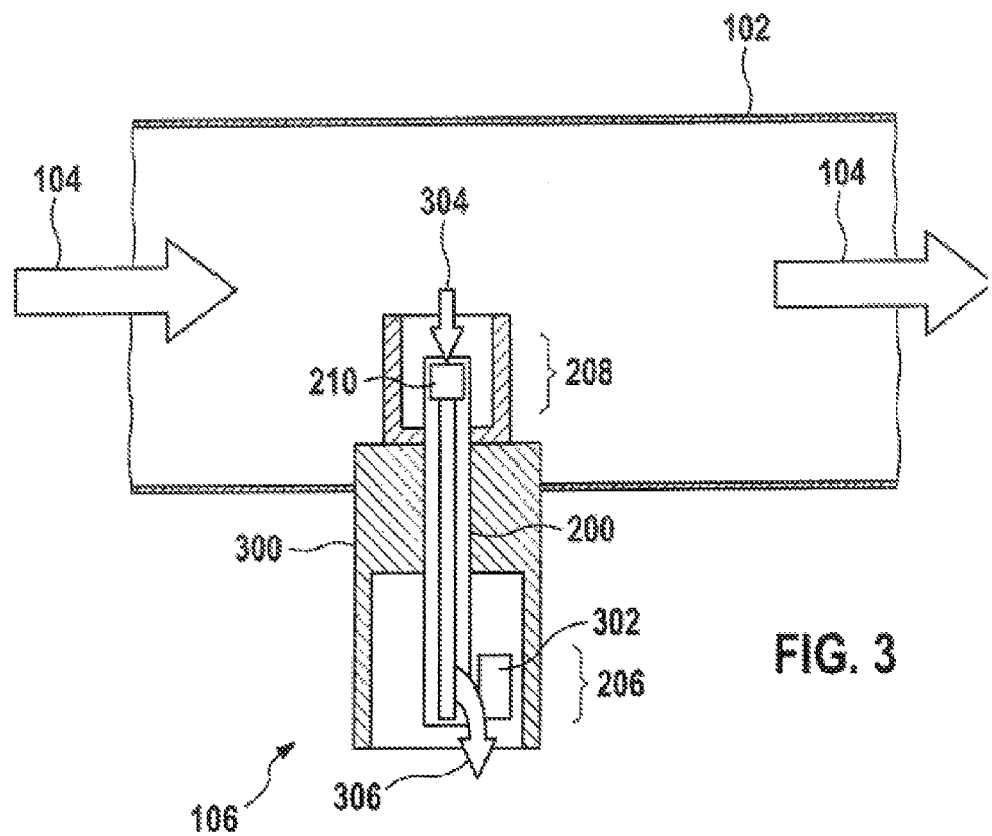
FIG. 3 shows a schematic illustration of an exhaust gas measuring device according to one exemplary embodiment of the present disclosure.

FIG. 3 shows a schematic illustration of an exhaust gas measuring device 300 according to one exemplary embodiment of the present disclosure. The exhaust gas measuring device 300 is arranged on a guide device 102 of the exhaust gas stream 104. The guide device 102 is designed for an exhaust gas stream 104 to flow through it. The exhaust gas measuring device 300 is arranged on the guide device 102 in such a way that a subsection of the exhaust gas measuring device 300 is arranged within the guide device 102 and a subsection of the exhaust gas measuring device is arranged outside the guide device 102. The exhaust gas measuring device 300 has an exhaust gas sensor housing 200 in which an exhaust gas guide element 200 is arranged. At least that subsection of the exhaust gas measuring device 300 which is arranged within the guide device 102 is designed to be resistant to high temperatures. The exhaust gas guide element 200 may be an exhaust gas guide element 200 as already described in FIG. 2. A sensor 302 is arranged in the measuring region 206 of the exhaust gas guide element 200. A portion 304 of the exhaust gas, which portion flows in the exhaust gas stream 104 through the guide device 102 for the exhaust gas stream 104, is conducted into the exhaust gas guide element 200 by means of the gas receiving element 210 which is arranged in the receiving region 208. That portion 304 of the exhaust gas which is conducted out of the exhaust gas stream 104 flows through the exhaust gas guide element 200 in order to be conducted past the sensor 302 in the measuring region 206 and to flow out of the exhaust gas guide element 200 as exhaust gas 306. Therefore, a portion 304 of the exhaust gas can be conducted through the exhaust gas guide element 200 from within the guide device 102 of the exhaust gas stream 104 to the outside of the guide device 102 of the exhaust gas stream 104.

In one exemplary embodiment of the exhaust gas measuring device 300, the sensor 302 and the gas receiving element 210 can be connected to one another by means of at least one electrical line which is integrated the exhaust gas guide element 200. When the gas receiving element 210 is connected to at least one electrical conductor in one exemplary embodiment, at least one property of the gas receiving element 210 can be changed using a signal which is transmitted by means of the at least one electrical line. In different exemplary embodiments, the gas receiving element 210 can be designed as a particle filter, a diffusion barrier or a pump element. Furthermore, in one exemplary embodiment, the gas receiving element 210 can, in a manner acting as a catalytic converter, catalytically convert that portion 304 of the exhaust gas which is conducted into the exhaust gas guide element 202.

One aspect of the presented disclosure is the combination of a gas-permeable element, that is to say the exhaust-gas guide element 200, in the exhaust gas, or the exhaust gas stream 104, with a chemical sensor 302, wherein the inflow 304 of gas into the exhaust gas guide element 200 takes place in the exhaust gas space, that is to say within the the guide device 102 of the exhaust gas stream 104, and the chemical sensor 302 is physically separate, for example is located at the outlet 306 of the exhaust gas guide element 200, with the result that said chemical sensor senses only the gas composition which passes through the exhaust gas guide element 200.

In other words, the exhaust gas guide element 200 allows physical and therefore also thermal separation of the miniaturized sensor element, or sensor 302, from functional elements for pretreating a partial quantity of exhaust gas which is to be detected, that is to say from the gas receiving element 210. As a result, it is possible to operate, for example, an oxidation-type catalytic converter or a getter material in the exhaust gas at a temperature of, for example, 700° C., and to detect the partial quantity of exhaust gas which is converted by this catalytic converter using a miniaturized sensor 302 at an operating temperature of, for example, 250° C. Similarly, it is possible to use filters with a large physical area on the exhaust gas side. It is also advantageous for the miniaturized chemical sensor 302 to no longer be exposed directly to the exhaust gas stream 104, but rather that it can be located outside the exhaust gas stream 104 and only specific, less harmful exhaust gas constituent parts can still reach said sensor 302, as a result of which the service life of said sensor is increased. By way of example, a sufficiently high pressure difference between the exhaust gas space and the sensor location can be generated, with the result that rapid throughflow of gas and therefore a high degree of sensor dynamics is possible.

FIG. 3 shows the basic design. On exhaust gas sensor housing 300, in which the exhaust gas guide element 200 is located as the gas-permeable support element, is located in the guide device 102 of the exhaust gas stream 104, also called exhaust gas tube. The exhaust gas guide element 200 is installed within the exhaust gas sensor housing 300 in such a way that untreated exhaust gas can only enter the upper region of the exhaust gas sensor housing 300 and therefore only reach the gas receiving element 210, which can also be called a functional element of the exhaust gas guide element 200, but not the lower region of the exhaust gas guide element 200 on which the chemical sensor 302 is located. Only exhaust gas which has been pretreated by the gas receiving element 210 can reach the chemical sensor element 302 within the gas-permeable exhaust gas guide element 200. Said gas stream 306 can flow out either back into the exhaust gas stream 104 or, as an alternative, to the ambient air.

The gas which is to be measured can flow through the exhaust gas guide element 200 either actively, for example through pump elements, or passively, for example through a suitable exhaust gas sensor housing 300, owing to a generated pressure difference in different exemplary embodiments. The gas-permeable exhaust gas guide element 200 can be produced using ceramic thick-film technology (for example on the basis of $ZrO_2$, $Al_2O_3$ or LTCC technology); similarly, the use of thin-film technology (for example Si-based) and MEMS process engineering for production is possible. In both technologies, it is possible to integrate channels, cavities, chambers, porous regions and conductor tracks as well as heating elements. In addition, the use of semi-finished products (for example metal or ceramic materials) is also possible, for example in the form of a small ceramic tube.

Variants of exemplary embodiments which are not shown in any more detail are described in the text which follows. In one exemplary embodiment, contact can be made with the chemical sensor element 302 and the gas receiving element 210 by conductor tracks which are integrated into the exhaust gas guide element 200. In an advantageous enhancement, the gas receiving element 210 can be connected directly to the sensor element 302 and therefore, for example, the functioning of the gas receiving element 210 on the exhaust gas guide element 200 can be controlled, regulated or measured by the sensor element 302 or signals can be further processed.

Extension of the gas-permeable exhaust gas guide element 200 beneath the gas outlet and the sensor element 302 can likewise be possible and advantageous, in order to allow electrical contact to be made in this region, for example, by means of a pluggable connection, similarly to the, for example, known contact-connection of commercially available Lambda probes.

The gas receiving element 210 can fulfill, in particular, one or more of the following functions: particle filtering;

diffusion barrier, for example by means of a porous medium or small openings;

catalytic conversion of exhaust gas constituent parts, for example by means of (possibly heated) catalytic converters; and capturing specific exhaust gas constituent parts by means of suitable getter substances, change in the temperature of the exhaust gas partial quantity by temperature supply/temperature discharge, pump element, actively or passively.

The chemical sensor element 302 can be, for example, a field-effect-based gas sensor on the basis of the materials Si, SiC, GaN; similarly, the use of miniaturized electrochemical sensor elements is likewise possible for example.

Since one aspect of the present disclosure allows considerably lower sensor temperatures than can occur in the exhaust gas, all chemical measuring principles which usually can be used only at temperatures clearly below maximum exhaust gas temperatures (up to above 1000° C. possible) are suitable in principle; in specific applications (for example stationary installations), sensors which require room temperature are also feasible; in the exhaust gas section of vehicles, it appears possible to realize sensor temperatures starting from 100° C. depending on the site of installation. The use of sensor elements which are produced using semiconductor process engineering also allows, in advantageous enhancements, the integration of a microelectronics system which is necessary, for example, for conditioning sensor signals. When an electronics system is combined with the sensor 302, or an electronics system is integrated into the sensor, the following functions can be realized directly on the sensor chip, that is to say sensor 302 with an integrated electronic circuit:

signal amplification;
signal filtering;
analog/digital conversion;
multiplexing and therefore actuating several different sensors;
linearizing the lambda step change characteristic curve;
offset calibration of the sensor characteristic curve; and
communication with sensor bus system.

On account of the low space requirement by the sensor chip and also depending on the design variant of the gas receiving element 210, the heating power requirement can be drastically reduced in comparison to conventional ceramic exhaust gas sensors. This in turn makes it possible for power to be supplied to the entire sensor (=sensor element+microelectronics system+heater) by means of the bus system.

For example, FIG. 3 shows a schematic diagram of a gas-permeable exhaust gas guide element 200 as a support element with a gas receiving element 210 as a functional element at the gas inlet and a miniaturized chemical sensor element 302 at the gas outlet.

As illustrated in FIG. 1 and FIG. 3, the presented exemplary embodiments can be combined with different gas sensors, such as lambda probe and $NO_x$, HC, particle and $NH_3$ sensors for example, for use in internal combustion engines, vehicles and stationary installations (for example wood-fired ovens etc.).

Figure 4:
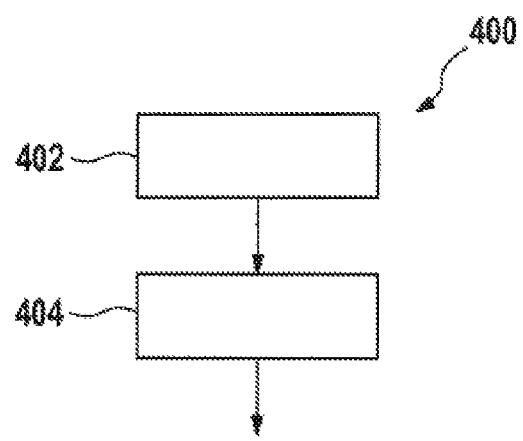
FIG. 4 shows a flowchart of a method for producing an exhaust gas guide element for conducting at least a portion of an exhaust gas to a sensor for a motor vehicle according to one exemplary embodiment of the present disclosure.

FIG. 4 shows a flowchart of a method 400 for producing an exhaust gas guide element for conducting at least a portion of an exhaust gas to a sensor for a vehicle according to one exemplary embodiment of the present disclosure. The method 400 comprises a provision step 402 and an arrangement step 404. In the text which follows, reference is made, for description, to the reference symbols used in FIG. 3 since said figure illustrates an exemplary embodiment of an exhaust gas guide element 200 of this kind. A gas receiving element 210 and also an exhaust gas guide element 200 are provided in the provision step 402. The exhaust gas guide element has a greater extent in a direction of a longitudinal axis 202 than in the direction of a transverse axis 204. In this case, the exhaust gas guide element 200 is gas-permeable in the direction of the longitudinal axis 202 and an end in the direction of the longitudinal axis 202 is designed as the receiving region 208, and the opposite end is designed as the measuring region 206, wherein, in particular, a sensor 302 can be arranged in the measuring region 206. In the arrangement step 404, the gas receiving element 210 is arranged in the receiving region 208 of the exhaust gas guide element 200.

The exemplary embodiments which have been described and shown in the figures are selected only by way of example. Entire or individual features of different exemplary embodiments can be combined with one another. An exemplary embodiment can also be supplemented by features of a further exemplary embodiment.

Furthermore, method steps according to the disclosure can be repeated and also executed in an order different to that described.

If an exemplary embodiment comprises an "and/or" link between a first feature and a second feature, this can be read as meaning that the exemplary embodiment has both the first feature and also the second feature according to one embodiment, and either only the first feature or only the second feature according to a further embodiment.

What is claimed is:

1. An exhaust gas guide element for conducting at least a portion of an exhaust gas to a sensor, wherein:
    a first extent of the gas guide element in a direction of a longitudinal axis is greater than a second extent of the gas guide element in a direction of a transverse axis;
    the exhaust gas guide element is configured to receive exhaust gas in the direction of the longitudinal axis;
    a first end of the gas guide element along the direction of the longitudinal axis is configured as a receiving region;
    a functional gas receiving element is positioned only in the receiving region; and
    a second end of the gas guide element opposite the first end is configured as a measuring region separate from said receiving region and from said gas receiving element and configured to receive a sensor positioned in the measuring region.

2. The exhaust gas guide element according to claim 1, wherein:
    the receiving region is configured to be positioned within a guide device of an exhaust gas stream;
    the measuring region is configured such that the measuring region is positioned outside the guide device when the receiving region is positioned within the guide device;
    the exhaust gas guide element is configured to conduct at least a portion of the exhaust gas from within the guide device to outside the guide device.

3. The exhaust gas guide element according to claim 1, wherein the exhaust gas guide element further includes at least one of a channel, a cavity, a chamber, a porous region, a conductor track, and a heating element.

4. The exhaust gas guide element according to claim 1, further comprising at least one electrical conductor, wherein at least one of the gas receiving element and a sensor positioned in the measuring region is electrically contacted using the electrical conductor.

5. The exhaust gas guide element according to claim 1, wherein the functional gas receiving element is configured as at least one of a particle filter, a diffusion barrier, a pump element, an element for converting a change in temperature of a portion of the exhaust gas conducted into the exhaust gas guide element, an element for capturing predetermined gas constituent parts, and an element for catalytically converting the portion of the exhaust gas conducted into the exhaust gas guide element.

6. An exhaust gas measuring device for a vehicle, comprising:
    an exhaust gas guide element configured to conduct at least a portion of an exhaust gas to a sensor, wherein:
    a first extent of the gas guide element in a direction of a longitudinal axis is greater than a second extent of the gas guide element in a direction of a transverse axis;
    the exhaust gas guide element is configured to receive exhaust gas in the direction of the longitudinal axis;
    a first end of the gas guide element along the direction of the longitudinal axis is configured as a receiving region;
    a functional gas receiving element is positioned only in the receiving region; and a second end of the gas guide element opposite the first end is configured as a measuring region separate from said receiving region and from said gas receiving element; and at least one of;
   a sensor positioned in the measuring region; and
   an exhaust gas sensor housing configured to be positioned in a guide device of an exhaust gas stream, wherein:

the exhaust gas guide element is positioned in the exhaust gas sensor housing;
   a subregion of the exhaust gas sensor housing comprising the receiving region is configured positioned in the exhaust gas stream;
   a further subregion of the exhaust gas sensor housing comprising the measuring region is configured arranged outside the exhaust gas stream when the subregion comprising the receiving region is positioned in the exhaust gas stream.

7. The exhaust gas measuring device according to claim 6, wherein the sensor is at least one of a field-effect-based gas sensor and an electrochemical sensor.

8. The exhaust gas measuring device according to claim 6, wherein a semiconductor sensor is positioned in the measuring region.

9. The exhaust gas measuring device according to claim 6, wherein the sensor is directly coupled to at least one of a microelectronics system and a microelectronic evaluation united integrated into the sensor.

\* \* \* \* \*